United States Patent [19]

Ricros et al.

[11] Patent Number: 4,736,851
[45] Date of Patent: Apr. 12, 1988

[54] PROCESS AND APPARATUS FOR THE AUTOMATIC INSPECTION BY TRANSPARENCY CONTRAST IN PARTICULAR OF CONTAINERS

[75] Inventors: Alain Ricros; Jean-Louis Blouin, both of Bordeaux; Jean-Paul Darnault, Talence; Yannick Pinson, Merignac, all of France

[73] Assignee: I2S, Bordeaux, France

[21] Appl. No.: 775,952

[22] Filed: Sep. 13, 1985

Related U.S. Application Data

[63] Continuation of Ser. No. 496,447, May 20, 1983, abandoned.

[30] Foreign Application Priority Data

May 27, 1982 [EP] European Pat. Off. ........ 82450008.6

[51] Int. Cl.⁴ ................................................ B07C 5/34
[52] U.S. Cl. ..................................... 209/524; 209/526; 209/939; 250/223 B; 356/240; 358/106
[58] Field of Search ................................ 209/522–526, 209/528, 565, 585, 587, 939; 382/27; 358/106, 213, 105, 139; 250/223 B; 356/240, 435, 394

[56] References Cited

U.S. PATENT DOCUMENTS

| 3,358,552 | 12/1967 | Schneider | 209/523 |
| 3,549,890 | 12/1970 | Keller | 250/209 |
| 3,932,042 | 1/1976 | Faani et al. | 209/585 |
| 3,963,348 | 6/1976 | Nakatani et al. | 209/524 |
| 4,280,624 | 7/1981 | Ford | 209/524 |
| 4,288,779 | 9/1981 | Otsu et al. | 382/27 |
| 4,327,375 | 4/1982 | Leclerc | 358/106 |
| 4,376,951 | 3/1983 | Miyazawa | 209/939 |
| 4,378,495 | 3/1983 | Miller | 250/223 B |
| 4,414,685 | 11/1983 | Sternberg | 382/27 |
| 4,454,541 | 6/1984 | Duschl | 358/106 |
| 4,454,542 | 6/1984 | Miyazawa | 209/526 |
| 4,488,648 | 12/1984 | Claypool | 209/526 |
| 4,492,476 | 1/1985 | Miyazawa | 358/106 |

FOREIGN PATENT DOCUMENTS 3035077 4/1982 Fed. Rep. of Germany .
2301006 9/1976 France .
2380551 9/1978 France .

Primary Examiner—Robert B. Reeves
Assistant Examiner—Donald T. Hajec
Attorney, Agent, or Firm—Schwartz, Jeffery, Schwaab, Mack, Blumenthal & Evans

[57] ABSTRACT

The invention concerns a process and an apparatus for automatic inspection of transparency contrast, consisting of illuminating the body of a container transversely to its axis (8), placing the container (3) against the light simultaneously with the aid of two charge transfer cameras, the sighting axes (11) of which are off-set angularly, of eliminating with the aid of an electronic window appropriate for each type of container, all signals originating in elementary points of the photosensitive matrix devices of said cameras (10) located outside the window, of analyzing successively each elementary point of the window by taking into account a predetermined number of immediately surrounding elementary points, of comparing the electric level of each elementary point weighted in this manner with a reference level pre-established for each type of container and of actuating the rejection of the container being inspected when the number of elementary points detected out of reference is higher than a predetermined number.

Application in particular to the inspection of bottles.

5 Claims, 2 Drawing Sheets

PROCESS AND APPARATUS FOR THE AUTOMATIC INSPECTION BY TRANSPARENCY CONTRAST IN PARTICULAR OF CONTAINERS

This application is a continuation, of application Ser. No. 496,447, filed May 20, 1983, now abandoned.

The present invention concerns the inspection by transparency contrast in particular of transparent or translucid containers, specifically of bottles, for detecting possible defects or foreign bodies inside the containers, or on or in the walls of said bottles.

More particularly, the invention concerns the inspection of empty bottles or the like, possibly containing defects or foreign bodies adhering to the wall or remaining inside, said bottles circulating on a conveyor for example of a bottling line, in order to eliminate automatically all defective bottles.

BACKGROUND OF THE INVENTION

There are already in existence different systems for the inspection by transparency contrast of parts of transparent or translucid containers, but none of them is capable at the present time of inspecting simultaneously the entirety of the parts of a container that may be analyzed by transparency contrast and to discriminate with sufficient precision and flexibility in any zone of the parts observed all defects, foreign bodies or contrast anomaly possibly constituting a cause of rejection of the container examined.

SUMMARY OF THE INVENTION

For this purpose, it is the object of the invention to provide a process for the inspection by transparency contrast of transparent or translucid containers, particularly bottles, characterized in that the process comprises illuminating the entirety or substantially the entirety of the body of the container to be inspected, transversely to its axis, placing the container against the light simultaneously with the aid of two charge transfer cameras the sighting axes of which are essentially perpendicular to the axis of the container, concurrent on said axis and forming between them an angle of several tens of degrees, eliminating with the aid of an electronic window appropriate for each type of container, all signals originating in the elementary points of the photosensitive recording means of said cameras located outside the window; analyzing successively each elementary point of the window by taking into consideration a predetermined number of elementary points of the immediate environment; comparing the electric level of each elementary point weighted with its immediate environment with a reference level established for each type of container and causing the rejection of the container inspected when the number of elementary points determined to be deviating from the reference by at least one of the two cameras is higher than a predetermined number.

The present invention also concerns an apparatus for the realization of the process described hereinabove, characterized in that it comprises displacement means capable of passing the containers to be inspected one by one in front of the source of illumination so as to illuminate them laterally, transversely to the axis of the containers, two charge transfer cameras placed on the other side of the path of the containers with respect to the source of illumination, with the sighting axes of said cameras being essentially concurrent on the axis of the container in the position of inspection, perpendicular to said axis and forming between them an angle of several tens of degrees, means to generate an electronic inspection window and superpose it on the image signals originating in the cameras so as to analyze only significant variations in the level of illumination within said inspection window, means to analyze sequentially the electric level of each elementary point of the photosensitive recording means of the two cameras by taking into account the level of the elementary points of the immediate environment, means to compare the level weighted in this manner of each elementary point with a predetermined adjustable reference level, means to count the number of elementary points considered to be deviating from the reference and means connected with the counting means to actuate an appropriate system for the rejection or marking of the container considered to be defective.

BRIEF DESCRIPTION OF THE DRAWINGS

The characteristics and advantages of the invention will become more apparent from the detailed description hereinafter given solely as an example, with regard to the drawings attached hereto, in which.

DESCRIPTION OF THE PREFERRED EMBODIMENTS

Figure 1:
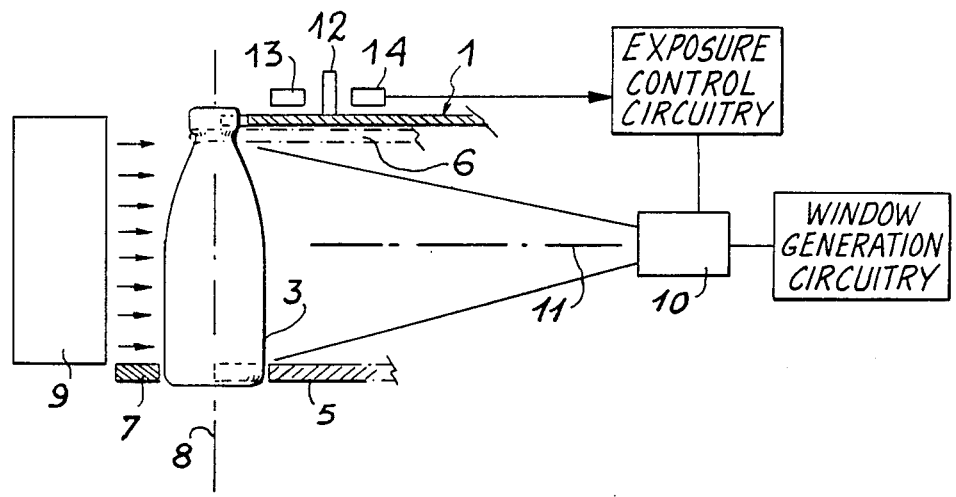
FIG. 1 shows schematically the mode of the analysis by transparency contrast of the body of a bottle according to the invention.
Figure 2:
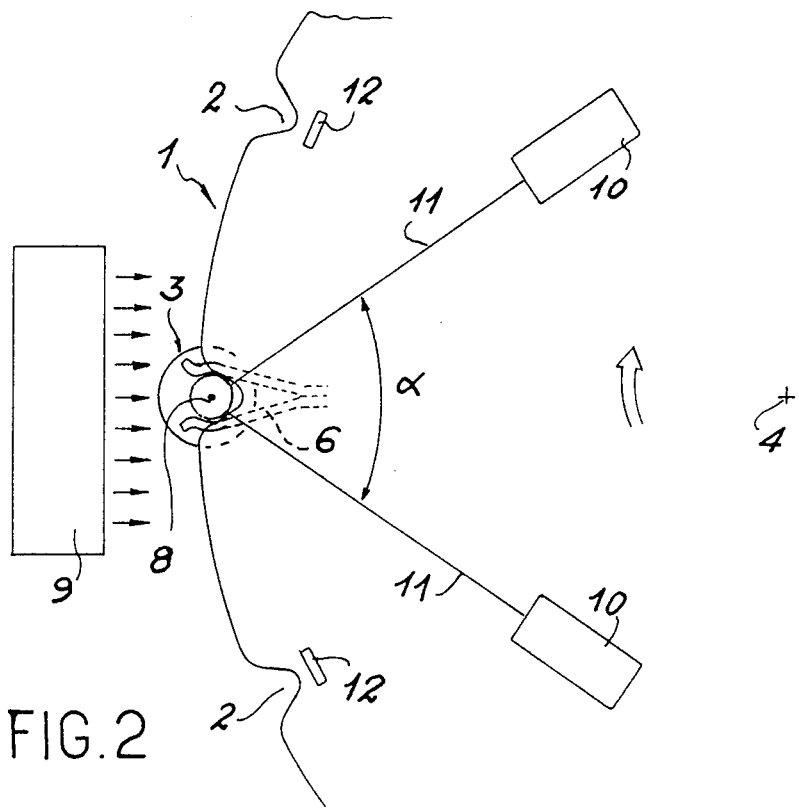
FIG. 2 shows a top view of the apparatus of FIG. 1.

FIGS. 1 and 2 display schematically at 1 a rotating star of a conventional type currently used in bottling lines. This device is inserted at one stage or another of processing and has the function of placing the containers one by one at an inspection, filling, capsuling, labelling, etc. station.

The device, shown in part, comprises in the usual manner a disk 1, notched regularly at its circumference at 2 to receive the neck of the bottles 3 to be treated.

The disk 1 has a vertical axis 4 and is rotated continuously by appropriate motor means, not shown.

Parallel to the star 1, a second star 5, integral with the first star and similarly notched at its circumference, is provided to receive the lower cylindrical end of the bottles.

The bottles 3 are maintained in place in their notches by a grip 6 mounted on the lower surface of the star 1 and associated with each notch 2, with such a grip seizing the neck directly under its upper bead, the bottles thus being in suspension during the time they are on the star 1. Such devices and their control means are known and will not be described in detail.

The lateral hold of the bottle at its lower part is completed by a stationary plate 7 in the shape of a circular arc, facing the star 5 and allowing just the free passage of the bottles.

The bottles 3 are thus moving in circular translation with their axis 8 vertical and are guided one by one to the inspection station according to the invention, consisting of a light box 9 mounted stationarily on one side of the path of the bottles 3 and two charge transfer cameras, also mounted stationarily, but on the other side of said path.

The light box 9 is placed so as to illuminate the body and the neck of the bottle 3. Preferably, the box 9 comprises a luminous screen diffusing the light in a uniform manner, with the plane of the screen being parallel to the axis 8 of the bottle and placed so that each camera 10 views the bottle 4 at the inspection station against the light.

The sighting axes 11 of the two cameras 10 are horizontal and intersect essentially on the axis 8 of the bottle, with the angle α included between the axes 11 amounting to several tens of degrees (between 70° and 100°, for example).

The means to present the bottles 3 at the inspection station are further equipped, in a known manner, with a position detection device consisting of the opaque index 12 fastened to the upper face facing star 1 of the each notch and capable of cutting the light beam of a stationary photoelectric detector placed to the right of the inspection station and comprising a source of light 13 and a photoelectric cell 14, the latter not being shown in FIG. 2 for the sake of clarity.

Figure 3:
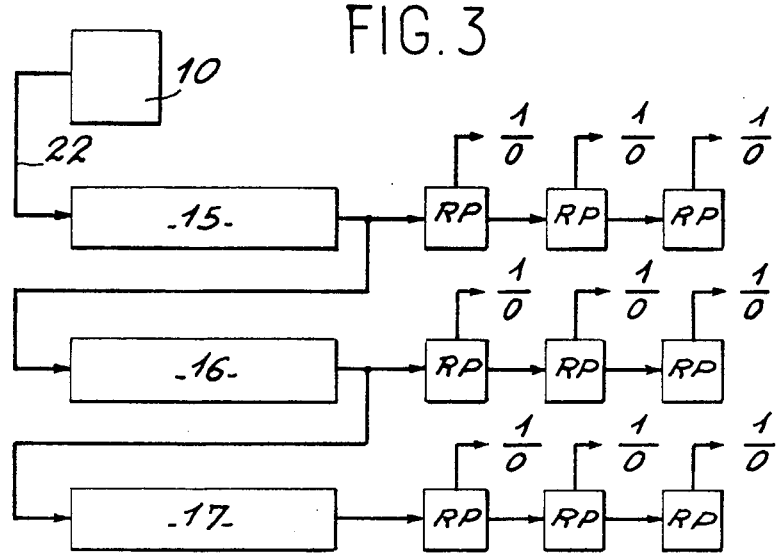
FIG. 3 is a functional diagram illustrating a part of the treatment of the video signals originating in the cameras and, FIG. 4 is a functional diagram illustrating the final phase of the treatment of said video signals.
Figure 4:
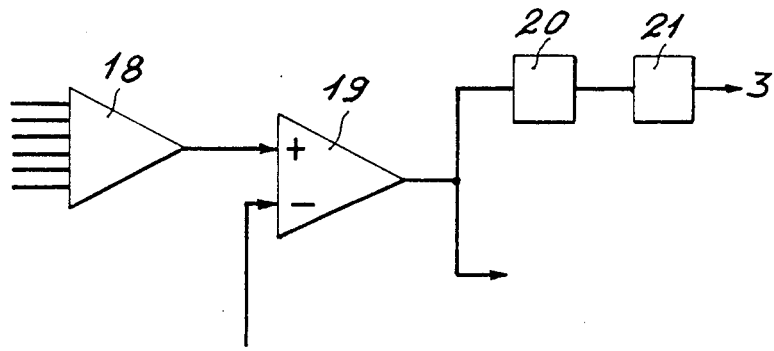

FIGS. 3 and 4 illustrate the chain of the electronic treatment of the video signals provided by the cameras 10. The figures show treatment by one camera, but in reality the signals of the two cameras are treated simultaneously in parallel by two systems identical with the one shown.

The video signals emitted by each camera 10 are passed to three shift registers 15, 16, 17 connected in line.

With each register 15, 16, 17, three in-line register points RP are associated, each effecting the comparison of the analog signal received with an adjustable threshold, so as to deliver a numerical information (1 or 0).

The numerical outlets of the register points RP are connected with an adder 18 (FIG. 4), the outlet of which is connected with one of the inlets of a comparator 19. The comparator 19 may or may not generate an output signal. If there is no signal, this indicates the absence of a defect or a foreign body (transparency); if there is a signal, it is passed to a counter 20, which upon the completion of a predetermined and adjustable count, actuates a device shown at 21 to reject or mark the bottle 3 just inspected.

The complete and detailed operation of the apparatus described hereinabove is as follows. The bottles 3 are brought, one after another, by the star 1 to the inspection station, where they are passed without stopping in front of the two cameras 10, which are actuated simultaneously by means of the photoelectric cell (12, 13, 14) to take a single image of each bottle.

For this type of charge transfer camera, the exposure time is of the order of 3 to 10 ms, so that the apparatus according to the invention is capable of handling passing velocities of up to 60,000 bottles per hour.

The range of the two cameras 10, off-set angularly by approximately 90°, makes it possible to cover for the purpose of transparency analysis the entire surface of the bottle 3, or at least the major portion of it, without any dead zones.

The charge transfer cameras comprise a photosensitive matrix device consisting of a certain number of elementary points (208 for example), which hereafter will be referred to as dots.

Briefly, the image is formed on the raster of dots and placed in memory on a grid on in-line shift registers.

At the level of each dot there is an electric charge proportional to the luminous flux and the charges accumulated by all of the dots during the exposure are transferred by successive shifts line by line to the memory.

The reading of the memory is effected by line by line and then point scanning so as to explore the entire photosensitive raster. For every point read, the quantity of the charge is converted into a proportional level of potential. These are analog signals which are delivered at 22 in FIG. 3 by the camera.

In summary, such a camera comprises an optical system, a sensor (a photosensitive matrix device), an electronic exposure control and reading system and an electronic video device which conditions and forms the output signal of the sensor in keeping with the standard of television signals.

According to the invention, the signals 22 coming from each camera 10 are passed to the set of shift registers 15 to 17. These registers contain as many points as the registers of the cameras (208, for example).

The last three informations of each registration 15 to 17 are memorized in three point registers RP. Thus, the video signals emitted by each camera are placed in memory by entire lines and at the outlet of the registers 15 to 17 the intensity levels of three consecutive points in a given column will appear.

The information placed in memory in the point registers RP are digitalized by comparison with a variable threshold adjusted as a function of the transparency of the type of bottle to be inspected. Each point register RP thus delivers a signal 0 or 1 corresponding to a white point (transparency) or a black point (not transparent) of the image of the bottle.

The point registers RP therefore provide binary information relative to a zone of 3×3=9 points of the image of the bottle by taking into account a zone extending over 9 dots, with said zone covering progressively the entire image.

The weighting of the level of each dot as a function of the eight dots immediately surrounding it is effected by means of an appropriate treatment algorithm as a function of the type of bottle, the material and the shape and nature of the foreign bodies or defects to be detected.

Such a weighting may be effected by program for example as a function of the average level of transparency of each container, the position in the image of the point under consideration and the position of each surrounding point relative to the point under consideration.

In order to eliminate any cause of outside disturbance potentially affecting the desired effect, a plurality of circuits incorporated in the treatment unit combined with the cameras 10 and not shown in the drawings, is charged in the usual and well known manner to generate an electronic inspection window defined by the configuration of the type of bottle to be inspected. Such a window is designed to take into account only signals originating in the dots located in the image zone of the bottle formed on the sensor of each camera 10.

It is understood that means are provided to pass from one type of window to another when the type of bottle to be inspected is changed.

All of the binary outlets of the point registers RP are connected with the adder 18 (FIG. 4) and the weighted average emitted by the adder 18 is compared with a programable numerical value in the comparator 19, which delivers a binary signal which for each dot considered, in view of its environment, is either 0 (the elementary zone of the bottle corresponding to the dot under consideration being taken as transparent in keeping with the criteria adopted), or 1 (the zone is question being considered nontransparent).

The binary signals 1 are counted in the counter 20, which, when the count attains a predetermined, variable threshold, issues a signal to the device 21 which consists either of a conventional system to reject the bottle just inspected, or a marking device permitting the subsequent removal of the bottle from the conveyor.

Preferably, it is provided that the counter 20 will count only consecutive signals of 1, with the counter being reset to zero if a 0 follows a 1, in order to ignore defects considered insignificant or too small in its dimensions.

Each camera 10 is followed by the treatment circuits shown in FIGS. 3 and 4, with the bottle inspected being rejected or marked is one of the two cameras, or both, "see" a foreign body or a defect.

The different comparison thresholds, together with the treatment algorithms mentioned hereinabove, make it possible to take into account and thus to consider as defects, or to not take into account all sorts of contrast anomalies due for example to scratches or traces of wear, pieces of a label or to foreign bodies adhering to the wall of the bottle or contained therein, liquid residues, spots, etc., according to highly variable "defect" criteria, which are readily adapted to each container to be inspected.

To facilitate the exploration of each object, an electronic exposure-lecture control system is provided, using the characteristics of a scanning charge transfer sensor.

This electronic system has the following effects:

actuating the integration of the image zone of the sensor at the precise moment of the passage of the object to be studied, which has the consequence of placing the images in which the objects to be analyzed are always located, at the same location from one exposure to the other, in combination with the use of an exploration window;

to coordinate the duration of the exposure of every image with the passage velocity of the objects in front of the camera, so as to reduce the blurring of the image while retaining good contrasts, to rapidly commit the image to the charge transfer memory so that the object image obtained in this manner may be reread at a velocity independent of the exposure time and a possible scanning cycle.

The simultaneous integration of the dots in such a sensor further permits the elimination of the phenomena of the distortion of the image of moving objects, well known in the case of conventional scanning cameras.

It should be noted that the invention may be applied to any transparent or translucid container but also generally to any transparent or translucent body capable of being inspected by transparency contrast in view of detecting possible defects, foreign bodies or other cause of transparency contrasts.

In the mode of embodiment described and shown hereinabove, scanning of the contents of the memory of the sensors of the cameras 10 has been provided by taking into account successively each dot and the eight dots surrounding it, but it should be understood that such a coverage may be either expanded or restricted by adjusting on the one hand the number of registers such as 15 to 17, or on the other, the number of register points such as RP, combined with each register, while the principle and methods of weighting remain unchanged. Such adjustments may be rendered necessary by the type of "defects" to be detected.

We claim:

1. Apparatus for the inspection by transparency contrast of transparent and translucent objects comprising:

displacement means for passing said objects along a path, one by one, to a predetermined inspection position in front of a source of illumination so as to illuminate said object laterally, transverse to a vertical axis of said object;

at least two charge transfer cameras each disposed on a side of the path opposite said source of illumination, said cameras having sighting axes convergent on said inspection position, means for actuating said charge transfer cameras upon the arrival of said objects at said inspection position such that each of said camera records a single image of said objects;

means for coordinating an exposure time of said charge transfer cameras as a function of the velocity of said objects;

means for generating an electronic inspection window so as to selectively analyze only significant variations in a level of illumination, detected by said cameras inside said inspection window;

photosensitive matrix means, disposed inside said cameras, having elementary points for instantaneously and simultaneously generating electric levels indicative of an image;

means for analyzing sequentially the electric level of each elementary point of said photosensitive matrix means inside said inspection window, wherein said analyzing means comprises a plurality of in-line shift registers, each shift register being coupled to a corresponding plurality of point registers, wherein each of said point registers compares the electric levels of particular ones of said elementary points with a variable predetermined adjustable threshold and generates a binary output signal indicative of the result of the comparison;

means for adding each of the binary output signals from said plurality of point registers and generating an output signal indicative of the total of the binary output signals;

means for comparing the output signal from said adding means with a predetermined threshold value and generating an output pulse signal when said output signal from said adding means exceeds said predetermined threshold value;

counting means for counting the number of output pulse signals generated by said comparing means and generating a defect signal when the number of counted output pulse signals exceeds a predetermined value; and means connected to said counting means for actuating a system to reject an object when said defect signal is generated by said counting means.

2. The apparatus of claim 1, wherein said means for actuating includes means for detecting the arrival of an object at said inspection station and means responsive to said means for detecting, for activating said cameras immediately upon said arrival such that each of said cameras records a single image of said object.

3. The apparatus of claim 2, wherein said means for detecting is a photoelectric cell.

4. The apparatus of claim 1, wherein the angle between the sighting axes of said cameras is between about 70 degrees and 100 degrees.

5. A method of inspecting transparency contrast of transparent and translucent objects comprising:
passing said objects along a path, one by one, to a predetermined inspection position in front of a source of illumination so as to illuminate said object laterally, transverse to a vertical axis of said object;
actuating at least two charge transfer cameras disposed on a side of the path opposite said source of illumination, said cameras having sighting axes convergent on said inspection position, the arrival of said objects at said inspection position such that each camera records a single image of said objects;
coordinating an exposure time of said charge transfer cameras as a function of the velocity of said objects;
generating an electronic inspection window so as to selectively analyze only significant variations in a level of illumination, detected by said cameras inside said inspection window;
simultaneously generating electric levels indicative of an image in a plurality of elementary points of a photosensitive matrix disposed inside each of said cameras;
analyzing sequentially the electric level of each elementary point of said photosensitive matrix inside said inspection window with an analyzing means, wherein said analyzing means comprises a plurality of in-line shift registers, each shift register being coupled to a corresponding plurality of point registers, wherein each of said point registers compares the electric levels of particular ones of said elementary points with a variable predetermined adjustable threshold and generates a binary output signal indicative of the result of the comparison;
adding each of the binary output signals from said plurality of point registers and generating an output signal indicative of the total of the binary output signals;
comparing the output signal indicative of the total of the binary output signals with a predetermined threshold value and generating an output pulse signal when said total of the binary output signals exceeds said predetermined threshold value;
counting means for counting the number of output pulse signals generated and generating a defect signal when the number of counted output pulse signals exceeds a predetermined value; and
actuating a system to reject an object when said defect signal is generated.

* * * * *